United States Patent [19]

Ruehl et al.

[11] Patent Number: 5,561,163
[45] Date of Patent: Oct. 1, 1996

[54] TREATING HEARING LOSS WITH DEPRENYL

[75] Inventors: William W. Ruehl, Lake Quivira; David R. Stevens, Leawood, both of Kans.

[73] Assignee: Deprenyl Animal Health, Inc., Overland Park, Kans.

[21] Appl. No.: 475,186

[22] Filed: Jun. 7, 1995

Related U.S. Application Data

[63] Continuation-in-part of Ser. No. 113,608, Aug. 27, 1993, Pat. No. 5,387,615, which is a continuation-in-part of Ser. No. 975,284, Nov. 12, 1992, Pat. No. 5,276,057, which is a continuation-in-part of Ser. No. 643,452, Jan. 18, 1991, abandoned, which is a continuation-in-part of Ser. No. 576,011, Aug. 31, 1990, Pat. No. 5,151,449.

[51] Int. Cl.$^6$ .................. A61K 31/135; A61K 31/13
[52] U.S. Cl. ............................. 514/654; 514/671
[58] Field of Search ..................... 514/671, 654

[56] References Cited

U.S. PATENT DOCUMENTS

| | | | |
|---|---|---|---|
| 4,564,706 | 1/1986 | Ecsery et al. | 564/376 |
| 4,861,800 | 8/1989 | Buyske | 514/646 |
| 4,871,550 | 10/1989 | Millman | 424/601 |
| 4,880,833 | 11/1989 | Knoll et al. | 514/565 |
| 4,916,151 | 4/1990 | Berg et al. | 514/419 |
| 5,192,808 | 3/1993 | Ruehl et al. | 514/654 |
| 5,276,057 | 1/1994 | Milgram | 514/654 |

FOREIGN PATENT DOCUMENTS

| | | |
|---|---|---|
| 871155 | 5/1971 | Canada. |
| 1215394 | 12/1986 | Canada. |

OTHER PUBLICATIONS

Milgram, et al., "Maintenance on L–Deprenyl Prolongs Life in Aged Male Rats", Life Sciences, vol. 47, 190, pp. 415–420 (1990).

Knoll, "Extension of Life Span of Rats by Long–Term (–)Deprenyl Treatment", The Mountain Journal of Medicine, vol. 55, No. 1, Jan. 1988, pp. 67–74.

Knoll, "The Striatal Dopamine Dependency of Life Span in Male Rats, Longevity Study with (–)Deprenyl" Mechanisms of Aging & Developments, 46, (1988), 237–262.

Knoll, "The Pharmacology of Selective Mao Inhibitors", Monoamine Oxidase Inhibitors—The State of the Art, 1981, pp. 45–67.

Knoll, et al., "Long–Lasting, True Aphrodisiac Effect of (–)Deprenyl in Sexually Sluggish Old Male Rats", Modl. Probl. Pharmacopsychiat, vol. 19, pp. 135, 153 (198 3).

*Primary Examiner*—Theodore J. Criares
*Attorney, Agent, or Firm*—Zarley, McKee, Thomte, Voorhees, & Sease

[57] ABSTRACT

Selegiline and pharmaceutically acceptable analog forms thereof are used as treatments for hearing loss in mammals, especially dogs.

5 Claims, No Drawings

TREATING HEARING LOSS WITH DEPRENYL

CROSS-REFERENCE TO A RELATED APPLICATION

This application is a continuation-in-part of Ser. No. 113,608 filed Aug. 27, 1993, now U.S. Pat. No. 5,387,615, which was a continuation of Ser. No. 975,284 filed Nov. 12, 1992, now U.S. Pat. No. 5,276,057, which was a continuation-in-part of Ser. No. 643,452 filed Jan. 18, 1991 (abandoned), which was a continuation-in-part of Ser. No. 576,011 filed Aug. 31, 1990 (U.S. Pat. No. 5,151,449).

BACKGROUND OF THE INVENTION

Hearing loss or impairment is a common occurrence for mammals. Impairment anywhere along the auditory pathway from the external auditory canal to the central nervous system may result in hearing loss. Auditory apparatus can be divided into the external and middle ear, inner ear and auditory nerve and central auditory pathways. While having some variations from species to species, the general characterization is common for all mammals.

Auditory stimuli are mechanically transmitted through the external auditory canal, tympanic membrane, and ossicular chain to the inner ear. The middle ear and mastoid process are normally filled with air. Disorders of the external and middle ear usually produce a conductive hearing loss by interfering with this mechanical transmission. Common causes of a conductive hearing loss include obstruction of the external auditory canal, as can be caused by aural atresia or cerumen; thickening or perforation of the tympanic membrane, as can be caused by trauma or infection; fixation or resorption of the components of the ossicular chain; and obstruction of the Eustachian tube, resulting in a fluid-filled middle-ear space.

Auditory information is transduced from a mechanical signal to a neurally conducted electrical impulse by the action of neuro-epithelial cells (hair cells) and first-order neurons (spiral-ganglion cells) in the inner ear. All central fibers of spiral-ganglion cells form synapses in the cochlear nucleus of the pontine brain stem. The auditory projections from the cochlear nucleus are bilateral, with major nuclei located in the inferior colliculus, medial geniculate body of the thalamus, and auditory cortex of the temporal lobe. Although the details of the neurophysiology of the inner ear and central auditory projections are beyond the scope of this review, a few specific observations are important for an understanding of the localization of hearing loss. First, the number of neurons involved in hearing increases dramatically from the cochlea to the auditory brain stem and the auditory cortex. All auditory information is transduced by a limited number of hair cells, of which the so-called inner hair cells, numbering a comparative few, are critically important, since they form synapses with approximately 90 percent of the primary auditory neurons. By comparison, at the level of the cochlear nucleus, the number of neural elements involved is measured in the hundreds of thousands. Thus, damage to a relatively few cells in the auditory periphery can lead to substantial hearing loss. Hence, many causes of sensorineural loss can be ascribed to lesions in the inner ear. This hearing loss can be progressive and is irreversible.

The hearing of pet animals, like that of humans, becomes significantly less acute because of changes in the anatomy of the ear as the animal ages. The anatomic basis for hearing loss in pet animals has received little attention. When hearing loss such as that herein-described occurs, the sum total of physiological events that occur is perceived by those observing the animal as inadequate behavioral response to sounds such as commands.

Of course, proper function of the individual components of the auditory system is important for pet owners to maximize the enjoyment of their pet. Like humans, pet animals that cannot hear do not adequately respond to environmental stimuli. Thus, the animal is often perceived as slow, "dumb", and not as fun as in its youth, when the true cause for these human perceptions is simply hearing impairment.

Use of mechanical hearing aids for animals is simply not practical for obvious reasons. There is, therefore, a need to treat hearing loss in animals such as dogs, cats, horses and other pets. This invention has as its primary objective the fulfillment of this continuing need.

Selegiline is a selective monoamine oxidase B (MAO-B) inhibitor, which is widely used as an adjunct in the treatment of Parkinson's disease. While its most common usage is for the treatment of Parkinson's disease, selegiline was originally developed as an antidepressant agent. Recent testing has indicated that selegiline may have some effect on increasing sexual response in aging animals, and also may have some effect, at least in rats, in increasing the natural life span. However, to date selegiline has only been medically approved by regulatory agencies for use for treatment of Parkinson's disease.

Like most drugs, selegiline can have diverse physiological effects which are completely dependent upon the dose administered. In accordance with the present invention, selegiline can be used for successful methods of treatment to provide the desired physiological effects enumerated herein, providing that it is used at the dosage levels mentioned herein, and providing it is administered at the periodic intervals and for the time spans mentioned herein. Obviously, when different dosages and levels of treatment are used, the results expressed herein may not be achieved. In fact, at higher doses adverse behavioral effects may be encountered.

SUMMARY OF THE INVENTION

The present invention relates to the process of using a known compound, selegiline, for new uses. In particular, at the dosage levels described herein, providing that the dosage is used for at least the periods of time expressed herein, there is an observed decrease in hearing impairment, and in fact in many cases an improvement in hearing is perceived, especially by pet owners. The treatment is especially useful for domesticated pets like dogs and cats but also would be expected to have utility in any mammalian species, such as horses and even humans.

DETAILED DESCRIPTION OF THE INVENTION

As earlier stated, the compound that is useful for the method or protocol of the present invention is a known compound, selegiline. Selegiline has the formula (−).N.α.dimethyl.N.2.propynylbenzene.ethanamine. It can be illustrated by the following graphic formula:

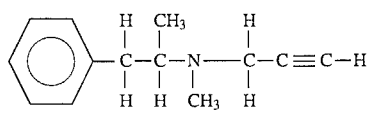

Selegiline also is at times referred to as 1-deprenyl to illustrate that it is a levorotary isomer which is the active form for treatment of Parkinson's disease. Typically, it is provided in a pharmaceutically acceptable salt form thereof such as the hydrochloride salt.

As used here, pharmaceutically acceptable salt form thereof means tile following. Acceptable for use in the pharmaceutical or veterinary art, being nontoxic or otherwise not pharmaceutically or veterinary unacceptable. "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the therapeutically active compound selegiline to achieve physiological results of the present invention can be via any of the accepted modes of administration for systemically active substances. These methods include oral, parenteral, and otherwise systemic, aerosol, and topical forms, as well as sustained release systems, etc.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenterals, and oral liquids, including oil aqueous suspensions, solutions and emulsions. It may include long-acting injectables and sustained release devices.

When the dosage is in solid form, solid pharmaceutical carrier such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate, in combination with citric acid, may be used to form the tablets.

Unit dosage forms such as tablets and capsules may contain any suitable predetermined amount of selegiline, advisably as a nontoxic acid additional salt, and may be administered one or more at a time at regular intervals as later described. Such unit dosage forms, however, should with a broad range guideline contain a concentration of 0.1% to 10% by weight of one or more forms of the active selegiline.

A typical tablet may have the composition:

|  | Mg. |
|---|---|
| 1. Selegiline | 10.0 |
| 2. Mannitol | 100 |
| 3. Stearic acid | 3 |

A granulation is made from the mannitol. The other ingredients are added to the dry granulation and then the tablets are punched.

Another tablet may have the composition:

|  | Mg. |
|---|---|
| 1. Selegiline | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|  | Mg. |
|---|---|
| 1. Selegiline | 5 |
| 2. Lactose U.S.P. | 200 |
| 3. Starch U.S.P. | 16 |
| 4. Talc U.S.P. | 8 |

As earlier expressed, physiological functions effected by the treatment herein with selegiline are necessarily dosage dependent. Put another way, like most drugs, selegiline has diverse physiological effects depending upon the dose administered. Unless the dose administered is within the levels set forth herein, the desired effect on hearing loss is not achieved without adverse effects.

While the tests later described herein are only provided for testing of dogs, the tests are a fair generalization for mammals. And therefore, the term mammal, as used herein, includes, without limitation, humans and domesticated animals such as cattle, horses, swine, sheep, dogs, cats, goats and the like. The tests are particularly illustrative for domesticated pets such as dogs and cats. The treatment may even work for birds or fish.

In accordance with the present invention, it has been demonstrated that hearing loss can be treated to slow hearing impairment, and in some cases improve hearing, if the animal is treated periodically with small, but therapeutically effective doses of selegiline. As explained hereafter, one can evaluate hearing loss by observing the animal's behavior in response to sounds, and when this is done in accordance with the regimen hereinafter described, the animal's behavior in response to sounds in its natural environment becomes significantly improved, even under artificial conditions in a clinic.

As hereinafter explained, the dosage regimen to achieve these desirable results shows usage at levels from about 0.01 mg/kg of body weight up to about 20 mg/kg of body weight from one to seven times weekly. Most preferably, the dosage level is 0.1–2.0 mg/kg of body weight given 1–7 times weekly. Of course, it would be known to those in the art that sustained release systems can be used to provide less frequent dosing to achieve the required dosage level.

It is not known precisely why the use of selegiline at the dosage levels and periodicity expressed herein achieves these results. It is simply not known by what mechanism the compound works, except to say that it is critically important that the dosage be at levels expressed herein; otherwise adverse effects may be achieved, particularly in dogs.

EXAMPLE

Fifty elderly pet dogs (>9 yrs.) of various breeds with geriatric onset hearing loss were presented by their owners for veterinary examination. The hearing of each dog was considered severely impaired and had deteriorated during the prior year, presumably due to degenerative changes as described above. In each dog, causes of hearing impairment due to conductive disorders, such as infection or other diseases of the external ear, were ruled out by careful physical examination. Systemic inflammatory or other debilitating disease was ruled out by physical examination and laboratory tests, including complete blood count and determination of a serum chemistry profile. Hence, the most likely cause of acquired hearing loss in these dogs was loss of structure or function of the hair cells or other sensorineural structures or neurons. Each dog was then treated once daily with 0.5 mg/kg selegiline orally, and re-evaluated monthly for 3 months and hearing was evaluated by routine methods. After one month of daily therapy with selegiline hearing was actually improved in 12 (24%) of the 50 dogs and further deterioration of hearing was prevented in 36 (72%) of the dogs; only 2 (4%) of the dogs studied deteriorated despite treatment. These results are statistically significant ($P<0.05$). Since age related hearing loss is a problem which gets progressively worse in an individual if left untreated, it is remarkable that 48 (96%) of the dogs studied either maintained or actually improved their hearing during the first month of treatment with selegiline.

These beneficial results were generally maintained for the duration of the study. After 3 months of selegiline therapy 33 dogs were available for re-examination, the other 17 being lost to follow-up. Compared to before the start of therapy, hearing was actually improved in 10 (30%) of the dogs and further deterioration had been prevented in 21 (64%) ($P<0.05$); in only 2 (6%) of the dogs had hearing deteriorated, These results demonstrate the effectiveness of selegiline for the treatment of hearing loss in mammals.

What is claimed is:

1. A method of treating hearing loss of mammals, comprising:
    administering to the mammal a small but hearing loss treating effective amount of the compound selegiline, or a pharmaceutically acceptable salt form thereof.
2. The method of claim 1 wherein the administering is of an oral dose.
3. The method of claim 1 wherein the selegiline is the hydrogen chloride addition salt form.
4. The method of claim 1 wherein the mammal is a dog.
5. The method of claim 1 wherein the hearing loss treating effective amount is from about 0.01 mg/kg of body weight to about 20 mg/kg of body weight.

* * * * *